United States Patent
Allen et al.

(10) Patent No.: US 7,301,044 B2
(45) Date of Patent: Nov. 27, 2007

(54) PREPARATION OF CHIRAL AMINO-NITRILES

(75) Inventors: David Robert Allen, La Grange Park, IL (US); Crystal A Achenbach-McCarthy, Lombard, IL (US)

(73) Assignee: Pfizer Inc., New York, NY (US)

(*) Notice: Subject to any disclaimer, the term of this patent is extended or adjusted under 35 U.S.C. 154(b) by 522 days.

(21) Appl. No.: 10/946,167

(22) Filed: Sep. 21, 2004

(65) Prior Publication Data

US 2005/0038281 A1     Feb. 17, 2005

Related U.S. Application Data

(63) Continuation of application No. 10/185,092, filed on Jun. 28, 2002, now abandoned.

(51) Int. Cl.
*C07C 255/03* (2006.01)
(52) U.S. Cl. .................................. 558/354
(58) Field of Classification Search ............... 558/354
See application file for complete search history.

(56) References Cited

OTHER PUBLICATIONS

P.G. Williams, W.Y. Yoshida, R.E. Moore, V.J. Paul, "Isolation and Structure Determination of Obyanamide, a Novel Cytotoxic Cyclic Depsipeptide from the Marine Cyanobacterium Lyngbya confervoides," J. Nat. Prod., 2002 (Published on Web Dec. 21, 2001), vol. 65, No. 1, pp. 29-31.

*Primary Examiner*—James O. Wilson
*Assistant Examiner*—Ebenezer Sackey
(74) *Attorney, Agent, or Firm*—Gregg C. Benson; Lisa A. Samuels

(57) ABSTRACT

A process and intermediates for producing 3-amino nitrites. The process involves resolving an enantiomeric mixture of chiral 3-amino nitrites in the presence of a chiral acid in a solvent system to produce a chiral 3-amino nitrile salt. The process may further comprise a recrystalizing step, wherein an enantiomerically enriched 3-amino nitrile salt is produced. The process may further comprise a salt exchanging step, wherein another acid is added to the chiral 3-amino nitrile salt or the enantiomerically enriched 3-amino nitrile salt to produce another 3-amino nitrile salt.

22 Claims, No Drawings

PREPARATION OF CHIRAL AMINO-NITRILES

FIELD OF INVENTION

This application is a continuation of U.S. application Ser. No. 10/185,092 filed Jun. 28, 2002, now abandoned.

The present invention relates to the production of chiral amino-nitrile compounds.

BACKGROUND OF THE INVENTION

Amino nitrites are organic compounds that have at least one amino group and at least one nitrile group. Amino nitriles have been found to be useful starting materials and intermediates for the production of fine chemicals.

One route for the production of amino nitrites is disclosed in Caputo et al, "Synthesis of Enantiopure N- and C-Protected homo-β-Amino Acids by Direct Homologation of the α-Amino Acids", Tetrahedron Letters, Vol. 51, No. 45, pp. 123337-12350, 1995. Caputo discloses the use of a triarylphosphine-iodine polymer bound complex in the presence of imidazole to replace the hydroxyl group with the iodo group and the subsequent displacement of the iodo group with a cyanide. The introduction of polymer bound reactants makes this methodology costly and undesirable. Moreover, Caputo utilized tetraethylammonium cyanide as a nucleophilic reagent and experienced significant deprotection of the amino group.

Another reaction scheme disclosed in Toujas, et al., Synthesis of homochiral N-Boc-β-aminoaldehydes from N-Boc-β-aminonitriles, Bull. Soc. Chim. Fr. (1997), 134(7), 713-717 utilizes costly solvents and results in low yields. Toujas, et al., discloses the N-Boc protection of the amino group and mesylation of the hydroxyl with methanesulfonyl chloride in the presence of triethylamine at room temperature. According to Toujas, et al., nucleophilic substitution with sodium cyanide in DMSO gives a relatively low yield of 56%.

The existing processes for producing useful amino nitrites have proven to be inefficient as multi steps are required and low yields are normally obtained.

SUMMARY OF THE INVENTION

The present invention provides a process for producing chiral amino nitrile compounds. Specifically, the process involves resolving an enantiomeric mixture of chiral 3-amino nitrites with a chiral acid in a suitable solvent system to produce a chiral 3-amino nitrile salt. The process may further involve a recrystalizing step to produce an enantiomerically enriched 3-amino nitrile salt from the chiral 3-amino nitrile salt. The process may further involve the step of exchanging the salt, wherein the chiral 3-amino nitrile salt or the enantiomerically enriched 3-amino nitrile salt is reacted with another acid to form another enantiomerically enriched 3-amino nitrile salt.

In one embodiment of the present invention, the enantiomeric mixture may include a racemic mixture of chiral 3-amino nitrites. In a specific embodiment, the racemic mixture of chiral 3-amino nitrites includes a racemic mixture of 3-aminopentanenitrile, which contains (R)-3-aminopentanenitrile and (S)-3-aminopentanenitrile. The solvent system may contain at least one solvent selected from ethyl acetate, toluene, and acetonitrile. The chiral acid may include a dibenzoyl-(L)-tartaric acid, which may be in monohydrate or anhydrous form.

The process of the present invention may yield a chiral 3-amino nitrile salt including (R)-3-aminopentanenitrile dibenzoyl-(L)-tartrate salt. This salt may be used as an intermediate for further modification.

In another embodiment, the process may further comprise the step of recrystalizing the chiral 3-amino nitrile salt in a recrystalizing solvent to form an enantiomerically enriched 3-amino nitrile salt. The recrystalizing solvent may be chosen from ethyl acetate, methyl ethyl ketone, isopropyl alcohol/water, acetonitrile, ethyl alcohol, methyl tert-butyl ether, dichloromethane/water, and tetrahydrofuran.

The recrystalizing step may yield an enantiomerically enriched 3-amino nitrile salt including (R)-3-aminopentanenitrile dibenzoyl-(L)-tartrate salt.

In another embodiment of the invention, the process further comprises a step of salt exchange, wherein another acid is added to the enantiomerically enriched 3-amino nitrile salt to produce another 3-amino nitrile salt. The other acid may include at least one of methanesulfonic acid and hydrochloric acid. The other 3-amino nitrile salt may include at least one of (R)-3-aminopentanenitrile methanesulfonic acid salt and (R)-3-aminopentanenitrile hydrochloric acid salt.

In an alternative embodiment, the recrystalizing step may be omitted, and the salt exchange step may be performed immediately after the resolving step.

Further, the present invention provides the compounds, namely, (R)-3-aminopentanenitrile dibenzoyl-(L)-tartrate salt and (R)-3-aminopentahenitrile dibenzoyl-(D)-tartrate salt. These compounds may be used as intermediates in the production of pharmaceutically active molecules.

In another embodiment of the invention, the process for preparing chiral 3-amino nitriles comprises the step of providing a compound, namely, (R)-3-aminopentanenitrile dibenzoyl-(L)-tartrate salt or (R)-3-aminopentanenitrile dibenzoyl-(D)-tartrate salt, and the step of exchanging the salt, wherein another acid is added thereto to produce another (R)-3-aminopentanenitrile salt. The other acid may include at least one of methanesulfonic acid and hydrochloric acid. The other (R)-3-aminopentanenitrile salt may include at least one of (R)-3-aminopentanenitrile methanesulfonic acid salt and (R)-3-aminopentanenitrile hydrochloric acid salt.

Other objects and further benefits of the present invention will become apparent to persons having ordinary skill in the art from the following written description and accompanying figures.

DETAILED DESCRIPTION OF THE INVENTION

For the purposes of promoting an understanding of the principles of the invention, specific language will be used to describe exemplary embodiments of the present invention. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides a process and intermediates for preparing useful 3-amino nitrile compounds. It has been known that only one enantiomer of certain chiral 3-amino nitrile compounds is particularly useful. For example, (R)-3-aminopentanenitrile, not (S)-3-aminopentanenitrile, is useful in the synthesis of pharmaceutically active molecules.

Enantiomeric mixtures as discussed herein contain two enantiomers. Further, enantiomeric mixtures that have equal amounts of two enantiomers are called racemic mixtures.

When enantiomers are separated, they cause the plane of polarized light to rotate by opposite but equal amounts. Optically active samples are those having an excess of one enantiomer over the other and thus showing a net rotation.

The present invention provides a process for preparing 3-amino nitrile compounds from an enantiomeric mixture containing two enantiomers, (R) and (S), of chiral 3-amino nitrile compounds. The enantiomeric mixture may be a racemic mixture, which contains approximately equal amounts of the (R) and the (S) enantiomers of chiral 3-amino nitriles.

The process of the present invention involves resolving the enantiomeric mixture in a solvent system in the presence of a chiral acid to produce a chiral 3-amino nitrile salt. During the resolving process, one particular enantiomer, preferably the (R) enantiomer, selectively reacts with the chiral acid to form an (R)-3-amino nitrile salt. The (S) enantiomer may occasionally react with the chiral acid to form an (S)-3-amino nitrile salt.

In order to determine the relative amounts of the (R)- and the (S)-3-amino nitrile salts, the product of the resolving step is analyzed using standard chiral and achiral liquid chromatography techniques. A high performance liquid chromatograph (HPLC) may be used to determine the relative proportions of each enantiomer. The result of the HPLC analysis may be used to determine the optical purity in terms of enantiomer excess (% ee), using the following calculation:

$$\%ee = \left(\frac{[\text{area \% major enantiomer} - \text{area \% minor enantiomer}]}{[\text{area \% major enantiomer} + \text{area \% minor enantiomer}]}\right) \times 100$$

A further identification of the product may be performed using a nuclear magnetic resonance (NMR) technique. The resolving step may yield a 3-amino nitrile salt having an optical purity of at least about 45% ee. In some experimental conditions, the optical purity of a desired 3-amino nitrile salt may reach between about 65% ee and about 95% ee.

The optical purity of the chiral 3-amino nitrile salt may be increased by means of a recrystalizing step. During the recrystalizing step, the chiral 3-amino nitrile salt is dissolved and recrystalized in a recrystalizing solvent. The recrystalizing solvent may be any suitable solvent that allows the chiral 3-amino nitrile salt to dissolve, and then crystalize at a lower temperature. The product of the recrystalizing step contains enantiomerically enriched 3-amino nitrile salt having an optical purity of at least about 89% ee.

The process of the present invention may further include a salt exchanging step, wherein the enantiomerically enriched 3-amino nitrile salt produced in the recrystalizing step is reacted with an acid to form a second 3-amino nitrile salt. The acid may be any strong acid that is capable of replacing the dibenzoyl tartrate group. For example, if the acid used is methanesulfonic acid, the salt produced is 3-amino nitrile methanesulfonic acid salt.

The salt exchanging step may be performed after the resolving step, without the recrystalizing step. An acid may be added to the 3-chiral amino nitrile salt, the product of the resolving step, to form a second 3-amino nitrile salt, such as a 3-amino nitrile methanesulfonic acid salt.

Specifically, the present invention provides a process for preparing the (R)-3-aminopentanenitrile dibenzoyl-(L)-tartrate salt ((R)-3-APN-DB-(L)-TA salt). The process may further involve a production of (R)-3-aminopentanenitrile methanesulfonic acid salt ((R)-3-APN-MSA salt) from the (R)-3-APN-DB-(L)-TA salt. The (R)-3-APN-MSA salt may be used in the production of pharmaceutically active molecules.

To initiate a process of the present invention, a racemic mixture of 3-aminopentanenitrile (3-APN), containing (R)-3-aminopentanenitrile ((R)-3-APN) and (S)-3-aminopentanenitrile ((S)-3-APN), is provided. Then 3-APN is resolved in a suitable solvent system in the presence of a chiral acid. The chiral acid may be a homochiral acid which contains only one enantiomer. In the process of the present invention, the chiral acid may include dibenzoyl-(L)-tartaric acid (DB-(L)-TA) and dibenzoyl-(D)-tartaric acid DB-(D)-TA).

It has been found that DB-(L)-TA is particularly reactive to (R)-3-APN, and DB-(D)-TA is particularly reactive to (S)-3-APN. Therefore, using DB-(L)-TA for resolving 3-APN results in (R)-3-aminopentanenitrile dibenzoyl-(L)-tartrate salt ((R)-3-APN-DB-(L)-TA salt) as a predominant product, while a small amount of (S)-3-aminopentanenitrile dibenzoyl-(L)-tartrate ((S)-3-APN-DB-(L)-TA salt) may be co-produced. Since one molecule of DB-(L)-TA binds to two molecules of 3-APN, the resulting (R)-3-APN-DB-(L)-TA salt is a di-salt.

Likewise, using DB-(D)-TA for resolving 3-APN will result in the (S)-3-APN-DB-(D)-TA salt as a predominant product, while a small amount of the (R)-3-APN-DB-(D)-TA salt may be co-produced.

Another chiral acid that may be used in resolving the enantiomers of 3-APN is di-p-toluoyl-(D)-tartaric acid. Like DB-(D)-TA, di-p-toluoyl-(D)-tartaric acid is particularly reactive to (S)-3-APN. Therefore, when di-p-toluoyl-(D)-tartaric acid is used in the resolving step, the predominant product is the (S)-3-aminopentanenitrile di-p-toluoyl-(D)-tartrate salt.

However, not all chiral acids are effective in resolving the enantiomers of 3-APN. For example, D-(−)-tartaric acid, (S)-(−)-malic acid, (R)-(−)-mandelic acid, and Z-L-Phenylalanine show very little selectivity towards either (R)-3-APN or (S)-3-APN. Therefore, when any of these particular chiral acid is used to resolve 3-APN, the resulting product contains approximately equivalent amounts of the (R) and the (S)-3-APN salts.

In addition, the solvent system may comprise at least one of ethyl acetate, water, toluene, and acetonitrile. Any combination and any proportion of the solvents may be effective in resolving 3-APN. Any other organic or aqueous solvent may also be used, however, the optical purity of the product may be enhanced with the use of an acetonitrile/water/ethyl acetate combination.

Further, the resolving step may require heating to allow 3-APN or the chiral acid to dissolve into solution. A temperature of between about 30° C. and about 80° C., may be suitable. However, an optimal temperature may be about 60° C. to about 65° C. After a specific time period, the reaction mixture may be cooled down to room temperature to allow salt formation.

The process of the present invention may further comprise recrystalizing the (R)-3-APN-DB-(L)-TA salt to produce an enantiomerically enriched (R)-3-APN-DB-(L)-TA salt. In the recrystalizing step, a recrystalizing solvent is added to the product of the resolving step, with stirring. The resulting mixture is heated to a temperature that allows the salt to completely dissolve. The solution is then cooled down to allow complete crystalization. The solids that are formed are collected, washed, dried and analyzed. The recrystalization process may yield a substantially pure product that contains at least about 89% ee of (R)-3-APN-DB-(L)-TA salt.

Further, the recrystalizing solvent may comprise at least one of ethyl acetate, methyl ethyl ketone, isopropyl alcohol/water, ethanol, methyl tert-butyl ether, dichloromethane/water, and tetrahydrofuran. Any suitable ratio of solvent to water may be used, however, a ratio of 5.6 solvent to 1 water has been shown to be effective in many cases.

Another step of the process involves exchanging the salt. During this step, the (R)-3-APN-DB-(L)-TA salt from the resolving step or the recrystalizing step is reacted with a strong acid such as methanesulfonic acid (MSA) to produce the (R)-3-APN-MSA salt, or hydrochloric acid to produce (R)-3-APN-HCl salt. The salt exchange step may be performed at room temperature. The reaction mixture may also be heated to an elevated temperature. Upon reaction completion, the reaction mixture can be cooled to room temperature. Solids formed upon cooling to room temperature can be recovered by filtration. The solids can be characterized by NMR and/or HPLC techniques.

The following non-limiting examples further demonstrate the present invention:

EXAMPLE 1

Resolving a Racemic Mixture of 3-APN with DB-(D)-TA

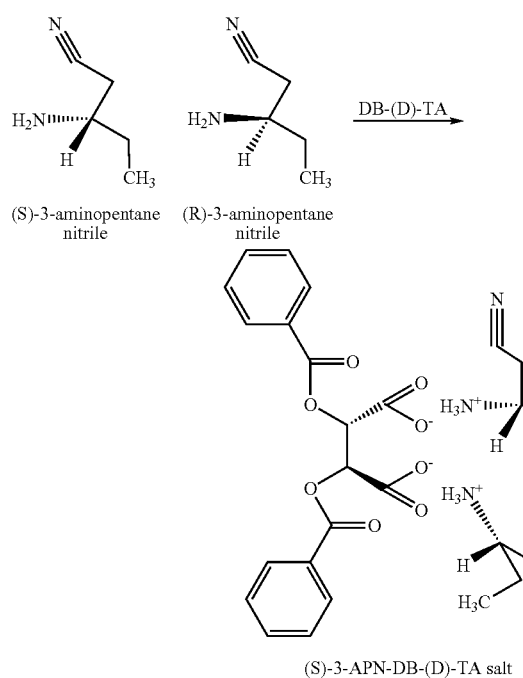

(S)-3-APN-DB-(D)-TA salt

A resolving step was initiated by charging 5 g (0.051 mol) of a racemic mixture of 3-APN to a round bottom flask. The mixture was diluted with a solution made of 20 mL of toluene and 10 mL of water. The diluted racemic mixture was heated to a temperature of 50° C. with stirring. Then, a solvent system made of 24 mL of toluene, 5 mL of water, and 11 mL of ethyl acetate, and containing 4.8 g (0.013 mol) of DB-(D)-TA monohydrate was slowly added to the diluted racemic mixture at a temperature of about 50° C. to form a reaction mixture. The maximum temperature reached about 65° C.

The reaction mixture was then cooled slowly to room temperature. After cooling the reaction mixture separated into an organic phase, an interface containing solids, and an aqueous phase. The solids from the interface were collected by filtration and allowed to air dry. A total of 3.46 grams of the dried solid was recovered. The aqueous phase was collected and concentrated to yield second solids, while the organic phase produced an oil product.

The results of the HPLC analysis showed that the solids from the interface layer were enriched with the (S)-3-APN-DB-(D)-TA salt, with an optical purity of 79.6% ee. The second solids from the aqueous phase, and the oil product from the organic phase were enriched with the (R)-3-APN-DB-(D)-TA salt, having an optical purity of 27.4% ee, and 26.4% ee, respectively.

EXAMPLE 2

Resolving a Racemic Mixture of 3-APN with DB-(L)-TA

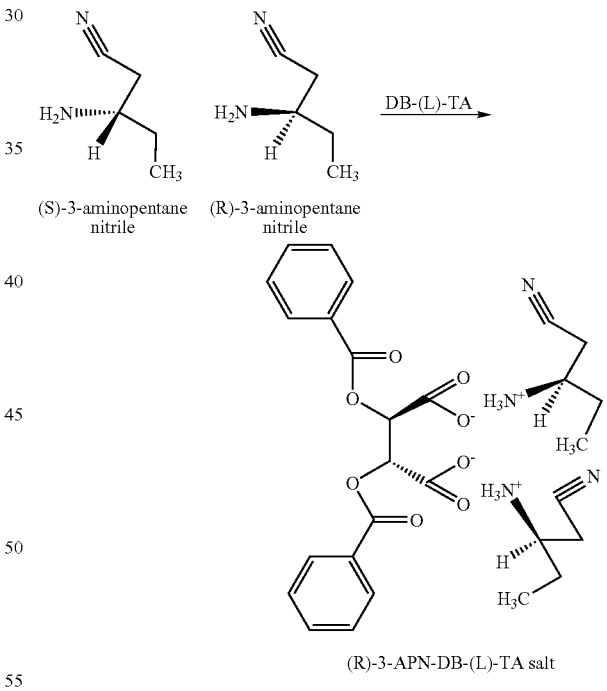

(R)-3-APN-DB-(L)-TA salt

An experiment was performed following the same experimental procedure described in EXAMPLE 1, except that DB-(L)-TA monohydrate was used instead of DB-(D)-TA monohydrate. The solids isolated from the interface layer in this experiment was determined to be enriched with the (R)-3-APN-DB-(L)-TA salt, having an optical purity of 79.3% ee. The yield of the solids was 3.43 grams. The identity of the (R)-3-APN-DB-(L)-TA salt was also confirmed by NMR. ($^1$H NMR (400 MHz), $D_2O$ δ=0.945 (t, 6H), 1.742 (m, 4H), 2.913 (d, 4H), 3.503 (m, 2H), 5.644 (s, 2H), 7.502 (t, 4H), 7.647 (t, 2H), 8.050 (d, 4H).)

Another experiment was conducted in order to improve the yield and the purity of the salt. In this experiment, 250 mL (227 g) of a racemic mixture of 3-APN was charged into a reaction vessel and diluted with 1230 mL of water. The solution was heated to a temperature of 65° C. Then, a solution, made of 680 mL of ethyl acetate, 128 mL of water, and 207 g of DB-(L)-TA, was added slowly over about 5-10 minutes to the diluted racemic mixture. The reaction mixture was immediately allowed to begin cooling slowly over approximately 3 hours until the mixture reached room temperature. The mixture was stirred for 4-5 hours at room temperature to allow for complete crystallization. Solids were collected by filtration, then washed twice with 100 mL of ethyl acetate and dried in vacuo at a temperature of about 45° C. The reaction yielded 118 g (36.7%) of the (R)-3-APN-DB-(L)-TA salt with an optical purity of 91.6% ee.

EXAMPLE 3

Resolving a Racemic Mixture of 3-APN with di-p-toluoyl-(D)-Tartaric Acid

A racemic mixture of 3-APN (0.55 mL, 0.5 g, 0.0051 mol) was diluted with water (2.7 mL) and heated to 60° C. A solution of di-p-toluoyl-(D)-tartaric acid (0.5 g, 0.0013 mol, 0.25 mole equivalents) in ethyl acetate (1.5 mL) and water (0.3 mL) was added. The reaction mixture was then cooled slowly to room temperature. The solids were isolated and dried. The yield of the solids was 0.42 g. As expected, the solids contained a higher proportion of the (S) enantiomer than the (R) enantiomer of the aminopentane nitrile di-p-toluoyl-(D)-tartrate salt. The area % ratio of R/S was 44.66/55.34.

EXAMPLE 4

DB-(L)-TA Experimentation

A racemic mixture of 3-APN was prepared as described in EXAMPLE 2. Two solvent systems were prepared, one containing an anhydrous form of DB-(L)-TA, and the other containing a monohydrate form of DB-(L)-TA. The racemic mixture was resolved in each case and the solids were collected and analyzed. The results (TABLE I) indicate that both the anhydrous form and monohydrate form of DB-(L)-TA worked to resolve the racemic mixture of 3-APN. The resulting (R)-3-APN-DB-(L)-TA salt had an optical purity of 89.14% ee (anhydrous form) and 92.00% ee (monohydrate).

TABLE I

Results of resolving step using different forms of DB-(L)-TA

| Form of DB-(L)-TA | 3-APN-DB-(L)-TA salt | |
|---|---|---|
| | area % ratio R/S | % ee R |
| Anhydrous | 94.57/5.43 | 89.14 |
| Monohydrate | 96.00/4.00 | 92.00 |

EXAMPLE 5

Optimization of Solvent System

Experiments were initiated by preparing a racemic mixture of 3-APN by charging 0.5 g of 3-APN into a reaction vessel, followed by the addition of a solution of toluene and water. The reaction vessel was heated to a temperature of 60° C. Then solvent systems were prepared by mixing at least one of ethyl acetate (EtOAc), water, toluene and acetonitrile (ACN) with about 0.27 mole equivalents of DB-(L)-TA. Each solvent system containing DB-(L)-TA was slowly added to the racemic mixture of 3-APN with stirring at the raised temperature and allowed to cool slowly to room temperature. The mixture may be chilled at 4° C. overnight to obtain a solid product. The solid product was collected by filtration, vacuum dried at a temperature about 40'-45° C., and analyzed by chiral HPLC. The results in TABLE II show that all the solvent systems tested yielded the products predominantly containing the (R)-3-APN-DB-(L)-TA salt. The optical purity of the (R)-3-APN-DB-(L)-TA salt ranged from 66.42% ee to 94.26% ee.

TABLE II

Products of resolving step using different solvent system

| | 3-APN-DB-(L)-TA salt | | |
|---|---|---|---|
| Solvent System | Yield (wt. %) | ratio area % R/S | % ee R |
| Toluene/water/ethyl acetate (2.6:1:1) | 56.4 | 84.21/17.79 | 66.42 |
| Toluene/water/ethyl acetate/acetonitrile (6.8:4.6:1:2) | 32.1 | 91.03/8.97 | 82.06 |
| Acetonitrile/water/ethyl acetate (2:11.4:1) | 1.3 | 97.13/2.87 | 94.26 |
| water/ethyl acetate (3.8:1) | 24.4 | 94.51/5.49 | 89.02 |

EXAMPLE 6

Recrystalizing of (R)-3-APN-DB-(L)-TA Salt

About 50 g of a crude product from the resolving step described herein above was slurried in 500 mL of ethyl acetate. The mixture was heated to 65-70° C. Then 90 mL of water was added and the diluted mixture was stirred at a temperature of about 65-70° C. until all solids dissolved (approximately 5-10 minutes). The heated mixture was cooled slowly to room temperature. Solids began forming when the temperature reached about 40-45° C. The cooled mixture was stirred at room temperature for 3-4 hours to allow for complete crystallization. The solids were collected by filtration, washed three times with 75 mL of ethyl acetate, and dried in vacuo at 45° C. This recrystallization process yielded 42 g (84.2% recovery) of substantially pure product containing the (R)-3-APN-DB-(L)-TA salt with an optical purity of 97.2% ee.

EXAMPLE 7

Experiments Using Alternative Recrystalizing Solvents

A 0.5 grams of the starting material containing 94.83% (R)-3-APN-DB-(L)-TA salt and 5.17% (S)-3-APN-DB-(L)-TA salt was stirred into 5.0 mL of an organic solvent and heated to 60° C. before being cooled to room temperature. In some cases, cooling to 4° C. was necessary before solids formed. The product from recrystalizing step was analyzed by chiral HPLC. The results (TABLE III) show that the optical purity of the (R)-3-APN-DB-(L)-TA salt could reach up to 100% ee, after the recrystalizing step.

TABLE III

Products of recrystalizing step using alternative recrystalizing solvent

| Recrystalizing Solvent | 3-APN-DB-(L)-TA salt area % ratio R/S |
|---|---|
| EtOAc | 94.93/5.07 |
| MEK | 96.73/3.27 |
| MEK/water(5.6:1) | 99.18/0.82 |
| IPA | 94.41/5.59 |
| IPA/water(5.6:1) | 99.30/0.70 |
| ACN | 95.82/4.18 |
| ACN/water(5.6:1) | 100.00/0 |
| EtOH | 95.91/4.09 |
| EtOH/water(5.6:1) | 99.86/0.14 |
| MTBE | 94.85/5.15 |
| MTBE/water(5.6:1) | 98.36/1.64 |
| DCM | 94.46/5.54 |
| DCM/water(5.6:1) | 96.51/3.49 |
| THF | 95.69/4.31 |
| THF/water(5.6:1) | 99.45/0.55 |
| DMF | no solids obtained |
| DMF/water | no solids obtained |

EXAMPLE 8

Production of (R)-3-APN-MSA Salt in a Salt Exchanging Step

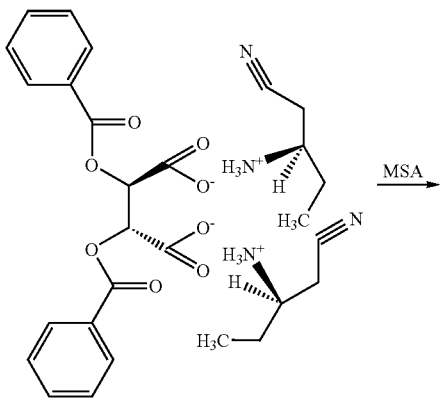

(R)-3-APN-DB-(L)-TA salt

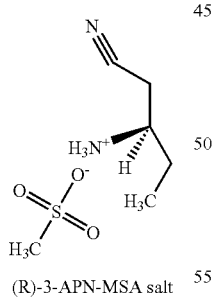

(R)-3-APN-MSA salt

The enantiomerically enriched (R)-3-APN-DB-(L)-TA salt (from recrystalizing step) (20 g) was slurried in 155 mL of ethyl acetate and heated to a temperature of about 65-70° C. About 4.7 mL of methanesulfonic acid (MSA) was added and the mixture was stirred at a temperature of about 65-70° C. until all solids dissolved. The solution was cooled to room temperature. Solids were collected by filtration, washed twice, each with 75 mL of ethyl acetate, and dried in vacuo at 45° C. The salt exchanging reaction yielded 13.78 g (98.5 wt. %) of (R)-3-APN-MSA salt with an optical purity of 97.3% ee.

Another experiment was performed to determine whether the salt exchanging step could be performed at room temperature. In this experiment, about 3 g (0.054 mol) of (R)-3-APN-DB-(L)-TA salt was slurried in 30 mL of ethyl acetate at room temperature. Then, about 0.71 mL (1.045 g, 0.0109 mol, 2.01 mole equivalents) of MSA was added to the slurry. The mixture was stirred at room temperature for 30-45 minutes. Solids were collected by filtration, washed twice with 20 mL of ethyl acetate, and dried in vacuo at 50° C. The yield of the salt was 1.99 g (94.8 wt. %).

While the invention has been illustrated and described in detail in the foregoing description, the same is to be considered as illustrative and not restrictive in character. It should be understood that only the exemplary embodiments have been shown and described and that all changes and modifications that come within the spirit of the invention are desired to be protected.

The invention claimed is:

1. A process for producing 3-amino nitrile compounds comprising the steps of:

providing an enantiomeric mixture of chiral 3-amino nitrites comprising:

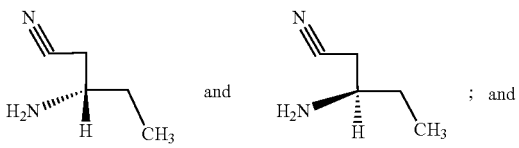

resolving said enantiomeric mixture of chiral 3-amino nitrites in the presence of a chiral acid in a solvent system to produce a chiral 3-amino nitrile salt.

2. The process of claim 1 wherein said enantiomeric mixture comprises a racemic mixture.

3. The process of claim 1 wherein said chiral acid comprises at least one of dibenzoyl-(L)-tartaric acid, dibenzoyl-(D)-tartaric acid, and di-p-toluoyl-(D)-tartaric acid.

4. The process of claim 3 wherein said dibenzoyl-(L)-tartaric acid comprises at least one of dibenzoyl-(L)-tartaric acid monohydrate, and dibenzoyl-(L)-tartaric acid anhydrous.

5. The process of claim 1 wherein said chiral acid comprises dibenzoyl-(L)-tartaric acid and said chiral 3-amino nitrile salt comprises (R)-3-aminopentanenitrile dibenzoyl-(L)-tartrate salt of the structure:

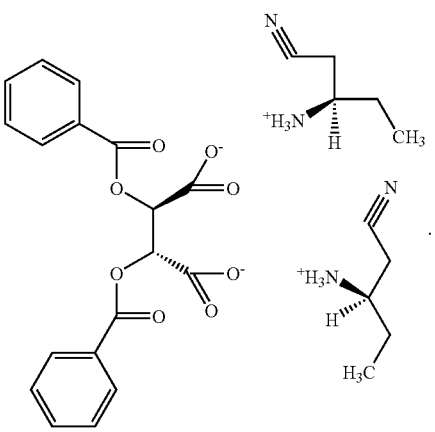

6. The process of claim 1 wherein said solvent system comprises at least one of ethyl acetate, toluene, acetonitrile, and water.

7. The process of claim 1 wherein said chiral 3-amino nitrile salt has an optical purity of at least about 45% ee.

8. The process of claim 7 wherein said chiral 3-amino nitrile salt has an optical purity of between about 65% ee and about 95% ee.

9. The process of claim 1 further comprising the step of: recovering said chiral 3-amino nitrile salt.

10. The process of claim 9 further comprising the step of: recrystalizing said recovered chiral 3-amino nitrile salt in a recrystalizing solvent to form an enantiomerically enriched 3-amino nitrile salt having an optical purity of at least about 89% ee.

11. The process of claim 10 wherein said enantiomerically enriched 3-amino nitrile salt comprises (R)-3-aminopentanenitrile dibenzoyl-(L)-tartrate salt of the structure:

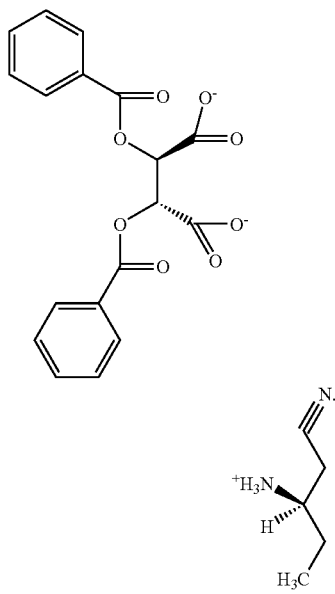

12. The process of claim 10 wherein said recrystalizing solvent comprises at least one of ethyl acetate, methyl ethyl ketone, isopropyl alcohol/water, acetonitrile, ethyl alcohol, methyl tert-butyl ether, dichloromethane/water, and tetrahydrofuran.

13. The process of claim 10 further comprising the step of: recovering said enantiomerically enriched 3-amino nitrile salt.

14. The process of claim 13 further comprising the step of: adding a strong acid to said enantiomerically enriched 3-amino nitrile salt to form a 3-amino nitrile salt of said strong acid.

15. The process of claim 14 further comprising the step of: recovering said 3-amino nitrile salt of said strong acid.

16. The process of claim 14 wherein said strong acid comprises at least one of methanesulfonic acid and hydrochloric acid.

17. The process of claim 14 wherein said other 3-amino nitrile salt comprises at least one of (R)-3-aminopentanenitrile methanesulfonic acid salt of the structure:

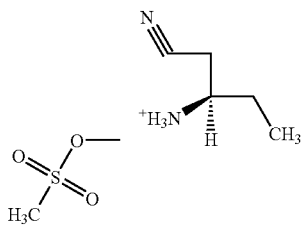

and (R)-3-aminopentanenitrile hydrochloric acid salt of the structure:

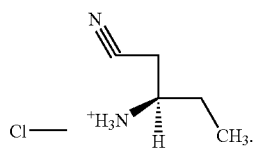

18. The process of claim 9 further comprising the step of: adding a strong acid to said chiral 3-amino nitrile salt to form a 3-amino nitrile salt of said strong acid.

19. The process of claim 18 further comprising the step of: recovering said 3-amino nitrile salt of said strong acid.

20. The process of claim 18 wherein said strong acid comprises at least one of methanesulfonic acid and hydrochloric acid.

21. The process of claim 18 wherein said other 3-amino nitrile salt comprises at least one of (R)-3-aminopentanenitrile methanesulfonic acid salt of the structure:

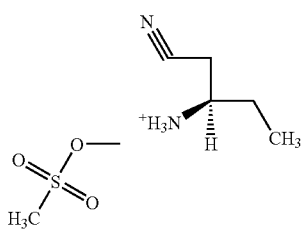

and (R)-3-aminopentanenitrile hydrochloric acid salt of the structure:

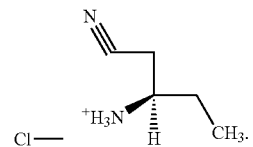

22. The chiral 3-amino nitrile salt produced by the process of claim 9.

* * * * *